United States Patent [19]

Carden

[11] Patent Number: 4,714,609

[45] Date of Patent: Dec. 22, 1987

[54] SKIN TANNING COMPOSITION

[75] Inventor: Anthony A. Carden, Fort Worth, Tex.

[73] Assignee: Laverne Stanley, Fort Worth, Tex.

[21] Appl. No.: 887,287

[22] Filed: Jul. 21, 1986

[51] Int. Cl.$^4$ ........................... A61K 7/42; A61K 7/44
[52] U.S. Cl. ........................................ 424/59; 424/60; 514/938
[58] Field of Search .............................. 424/59, 60, 63

[56] References Cited

U.S. PATENT DOCUMENTS

| | | | |
|---|---|---|---|
| 2,267,200 | 12/1941 | Hersberger et al. | 424/59 |
| 2,664,383 | 12/1953 | Fox et al. | 424/59 |
| 2,987,446 | 6/1961 | Riethmüller | 424/59 |
| 3,030,275 | 4/1962 | Kreps et al. | 424/59 |

OTHER PUBLICATIONS

Pharmaceutical Formulas, 1953, vol. I, pp. 145, 146, 150, 151, 220, 546, 684, 775, 786 to 788, 807, 808 and 835.
Sagarin, Cosmetics Science and Technology, 1957, pp. 750, 758 to 761, 764 to 767.
Martindale, The Extra Pharmacopoeia, 1958, 24th edition, pp. 1173 and 1174.

*Primary Examiner*—Dale R. Ore
*Attorney, Agent, or Firm*—H. Dennis Kelly; Charles D. Gunter, Jr.

[57] ABSTRACT

A composition of matter and method are shown for tanning the human epidermis. The composition comprises a base or carrier and an effective amount of vanillin. The vanillin reacts with proteins in the human epidermis, when exposed to the sun's rays to accelerate tanning.

2 Claims, No Drawings

4,714,609

SKIN TANNING COMPOSITION

BACKGROUND OF THE INVENTION

1. Field of the Invention

This invention relates to novel, unobvious, and useful compositions of matter and methods for tanning the human epidermis.

2. Description of the Prior Art

The tanning of human epidermis by the sun's rays depends greatly upon the complexion of the individual with some persons being much more sensitive to the sun's rays than others. Persons with a fair complexion may have difficulty in obtaining a tan. Many persons with fair complexions burn, and, therefore must restrict their exposure to the sun. Despite the problems which may be encountered by some in obtaining a tan, a great many people desire to tan the skin for cosmetic purposes. Unfortunately, this desire can result in medical problems, the most notable being skin cancer.

One proposed solution to the problem has been the use of compositions which act to screen out harmful rays of the sun. Accordingly, sunscreen compositions are known, such as those which contain compounds which absorb ultraviolet radiation in the range of 290–320 nm. These products have the advantage of preventing burning but do not promote tanning and offer only temporary protection.

Another product available to satisfy the cosmetic desires of individuals without incurring the undesirable effects of sun rays are the so called skin coloring or skin staining products. These products typically contain a chemical such as dihydroxyacetone, which darkens the skin by interacting with the keratin in the skin. Skin coloring agents of this type do achieve darkening of the skin, however a natural color is difficult to achieve, the color may not be even, and the color may be removed by washing in some instances. The use of chemical agents such as dihydroxyacetone is also offensive to those persons desiring to use a product with a "natural" tanning agent.

There exists a need, therefore, for a preparation to produce a natural-appearing tan which helps to accelerate the tanning process to thereby reduce the amount of exposure to the sun's rays necessary to achieve an even tan.

A need also exists for such a preparation which is non-allergenic and which utilizes a natural active ingredient to accelerate the tanning process.

SUMMARY OF THE INVENTION

The subject invention provides a non-allergenic tanning composition containing a natural active ingredient to accelerate the tanning process. The composition can be applied to the human epidermis to achieve a desired cosmetic effect in a shortened period of time to avoid over-exposure to the sun's rays. More specifically, the subject invention concerns the use of vanillin as the active ingredient in a tanning composition, the tanning composition including a cosmetic base such as a lotion, a cream, or an ointment. The cosmetic base can be, for instance, mineral oil.

DESCRIPTION OF THE PREFERRED EMBODIMENT

The term "Maillard Reaction" is a term applied by those in the food industry to describe a natural process in which aldehydes react with molecules containing amines to produce what is referred to as a "carbonyl-amine" reaction. A familiar example is a cut fruit, such as an apple, which begins to turn brown as the "carbonyl-amine" reaction occurs. The present invention is the discovery that vanillin, an aromatic aldehyde present in vanilla extract, can react with the free amine groups in the outer layers of the human skin to accelerate tanning when the skin is exposed to sunlight. To applicant's knowledge, the previously described carbonyl-amine reaction has never before been applied in cosmetic products for the purpose of accelerating the tanning of the human skin.

The sun tanning compositions of the invention comprise a base or carrier for the vanillin which base can be a lotion, a cream, or an ointment. The preferred base is mineral oil, i.e. highly refined petroleum oil, also referred to as "white oil", medicinal oil or cosmetic oil. Such oils are well known to those in the cosmetic industry and are commercially available.

The vanillin is preferably provided in the form of common vanilla, sometimes referred to as "vanilla extract." The Merck Index, 9th edition (1976) lists "vanilla" as being approximately 2 to 2.75% by weight vanillin, 4% by weight resin, 10% by weight sugar, and the balance vanillic acid.

The vanilla is present in the range from about 10 to 40% by weight, based on the weight of the total composition, preferably in the range from about 20 to 30% by weight, most preferably about 25% by weight, the chief remaining ingredient being mineral oil. A most preferred composition contains approximately 74% mineral oil and 24.7% vanilla, the balance being made up of conventional tanning ingredients. In the most preferred case, the conventional ingredients included octyl dimethyl PABA, benzophenone-3, water, sodium laureth sulfate, sodium lauryl sulfate, lauramide DEA, cocamidopropyl betaine, disodium monooleamido MEA sulfosuccinate, cocamidopropyl dimethylamide oxide, DMDM and Hydantoin. The ratio of mineral oil to vanilla employed in the composition of the invention is most preferably about 4:1, whatever other ingredients are used.

It will be understood by those skilled in the art that the cosmetic base could also constitute other known bases suitable for external (topical) application directly to the human skin. For example, an ointment base can be prepared by mixing (by weight) 10.0 parts of glyceral monosterate, 10.0 parts of cetyl alcohol, 30 parts of spermaceti, 10.0 parts of Span 20 (sorbitan monolaurate), 10.0 parts of Tween 20 (polyoxyalkylene derivative of sorbitan monolaurate), 12.5 parts of glycerin and 100 parts water. The resulting base can be compounded with an appropriate amount of vanillin as disclosed above. A lotion base can be prepared by mixing about 50% alcohol, 1% acetone, and 45% water, and the vanillin can be added to the lotion base, as discussed.

Various known sunscreening agents can be compounded with the base and vanillin, for instance, alpha-tocopherol orthoacetylsalicylate, homomenthyl silicylate, butyl benzal acetone oxalate, acetanilide, benzyl salicylate, oxynaphthoic acid, dimethyl aminobenzoic acid, phenyl salicylate and the like, all of which function to filter out the actinic rays from the sun. Other conventional ingredients can be included in the final composition.

The invention has been shown in only one of its forms. It should be apparent to those skilled in the art that it is not so limited, but is susceptible to various changes and modifications without departing from the spirit thereof.

I claim:

1. A method of tanning the human epidermis which comprises applying to said epidermis a composition comprising a cosmetic base, and an effective amount of vanillin, the vanillin being present in an amount effective to react with the skin epidermis to produce a carbonyl-amine reaction which results in accelerated tanning of the epidermis upon exposure to the sun's rays.

2. A method of tanning the human epidermis which comprises applying to said epidermis a composition comprising a cosmetic base made up of mineral oil and vanillin supplied in the form of vanilla extract, the vanilla extract containing approximately 1 to 4% by weight vanillin as the active ingredient, and the vanilla extract being present in the composition in the range from about 5 to 50% by weight, based on the total weight of the composition, to react with the skin epidermis to produce a carbonyl-amine reaction which results in accelerated tanning of the epidermis upon exposure to the sun's rays.

* * * * *